US010682176B2

(12) United States Patent
Fang et al.

(10) Patent No.: US 10,682,176 B2
(45) Date of Patent: Jun. 16, 2020

(54) SYSTEM AND METHOD FOR CONTROLLING CATHETER POWER BASED ON CONTACT FORCE

(71) Applicant: Biosense Webster (Israel) Ltd., Yokneam (IL)

(72) Inventors: Itzhak Fang, Irvine, CA (US); Garth Constantine, Murrieta, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1026 days.

(21) Appl. No.: 14/835,413

(22) Filed: Aug. 25, 2015

(65) Prior Publication Data

US 2017/0056103 A1    Mar. 2, 2017

(51) Int. Cl.
*A61B 18/14* (2006.01)
*A61B 90/00* (2016.01)
*A61B 18/00* (2006.01)

(52) U.S. Cl.
CPC ........... *A61B 18/1492* (2013.01); *A61B 2018/00357* (2013.01); *A61B 2018/00577* (2013.01); *A61B 2018/00666* (2013.01); *A61B 2018/00702* (2013.01); *A61B 2018/00708* (2013.01); *A61B 2018/00773* (2013.01); *A61B 2090/064* (2016.02); *A61B 2090/065* (2016.02)

(58) Field of Classification Search
CPC .......... A61B 18/1492; A61B 2090/065; A61B 5/6885; A61B 2090/064; A61B 2018/00702; A61B 2018/128; A61B 2018/00666
See application file for complete search history.

(56) References Cited

U.S. PATENT DOCUMENTS

| 6,226,542 | B1 | 5/2001 | Reisfeld |
| 6,241,724 | B1 | 6/2001 | Fleischman et al. |
| 6,301,496 | B1 | 10/2001 | Reisfeld |
| 6,695,808 | B2 | 2/2004 | Tom |

(Continued)

FOREIGN PATENT DOCUMENTS

| EP | 2047797 A2 | 4/2009 |
| EP | 2449996 A2 | 9/2012 |

OTHER PUBLICATIONS

EPO Search Report for EP Application No. 16185548.1 dated Jan. 31, 2017, 8 pages.

*Primary Examiner* — Linda C Dvorak
*Assistant Examiner* — Ryan T Clark

(57) ABSTRACT

A method for controlling an ablation power applied to a catheter includes: receiving, by a controller, a detected contact force from a sensor assembly of the catheter, the sensor assembly being configured to detect a contact force applied to the electrode; controlling, by the controller, a power supplied to an electrode of the catheter to have a deactivated power level when the detected contact force is less than a first threshold contact force; controlling, by the controller, the power supplied to the electrode of the catheter to have a first power level when the detected contact force is greater than the first threshold contact force; and controlling, by the controller, the power supplied to the electrode of the catheter to have a deactivated power level when the detected contact force is greater than a cutoff contact force, the cutoff contact force being greater than the first threshold contact force.

18 Claims, 14 Drawing Sheets

(56) References Cited

U.S. PATENT DOCUMENTS

| | | | |
|---|---|---|---|
| 6,814,733 B2 | 11/2004 | Schwartz et al. | |
| 6,892,091 B1 | 5/2005 | Ben-Haim et al. | |
| 6,915,149 B2 | 7/2005 | Ben-Haim | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 8,162,935 B2 | 4/2012 | Paul et al. | |
| 8,357,152 B2 | 1/2013 | Govari et al. | |
| 8,478,383 B2 | 7/2013 | Bar-Tal et al. | |
| 8,900,229 B2 | 12/2014 | Govari et al. | |
| 8,926,604 B2 * | 1/2015 | Govari | A61B 18/1492 606/34 |
| 2008/0161796 A1 | 7/2008 | Cao et al. | |
| 2010/0121138 A1 | 5/2010 | Goldenberg et al. | |
| 2010/0168620 A1 | 7/2010 | Klimovitch et al. | |
| 2012/0041295 A1 | 2/2012 | Schultz | |
| 2012/0108988 A1 * | 5/2012 | Ludwin | A61B 18/1492 600/508 |
| 2012/0165669 A1 | 6/2012 | Barley et al. | |
| 2012/0220999 A1 * | 8/2012 | Long | A61B 18/1206 606/41 |
| 2013/0296850 A1 * | 11/2013 | Olson | A61B 18/1492 606/41 |
| 2014/0187917 A1 | 7/2014 | Clark et al. | |
| 2014/0303551 A1 * | 10/2014 | Germain | A61B 17/22 604/30 |
| 2016/0029998 A1 * | 2/2016 | Brister | A61B 5/6853 600/424 |

\* cited by examiner

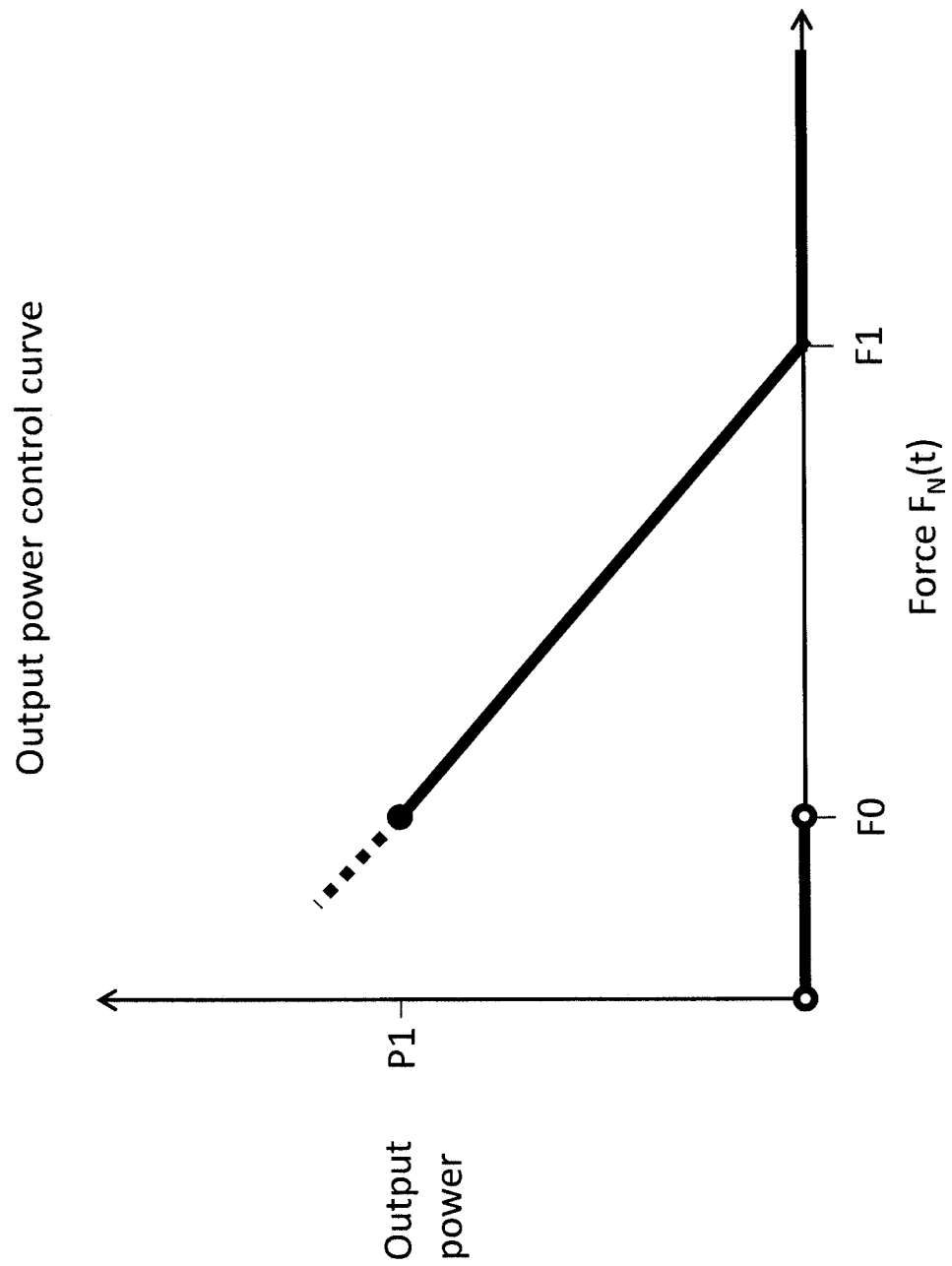

SYSTEM AND METHOD FOR CONTROLLING CATHETER POWER BASED ON CONTACT FORCE

FIELD

Aspects of embodiments of the present invention relate to invasive medical devices and associated control systems capable of sensing pressure exerted against a probe, such as a catheter, and control systems capable of adjusting the power supplied to the probe based on the sensed pressure.

BACKGROUND

In some diagnostic and therapeutic techniques, a catheter is inserted into a chamber of the heart and brought into contact with the inner heart wall. For example, intracardiac radio-frequency (RF) ablation is a known method to treat cardiac arrhythmias. In this technique, a catheter having an electrode at its distal tip is inserted through the patient's vascular system into a chamber of the heart. The electrode is brought into contact with a site (or sites) on the endocardium, and RF energy may be applied through the catheter to the electrode in order to ablate the heart tissue at the site. Excessive contact force (or pressure) and/or excessive RF energy, however, may cause undesired damage to the heart tissue and even perforation of the heart wall. As such, proper contact between the electrode and the endocardium is necessary in order to achieve the desired diagnostic function and therapeutic effect of the catheter.

Various techniques exist for verifying electrode contact with tissue. For example, U.S. Pat. No. 6,695,808, whose disclosure is incorporated herein by reference, describes apparatus for treating a selected patient tissue or organ region. A probe has a contact surface that may be urged against the region, thereby creating contact force or contact pressure. A pressure transducer measures the contact pressure and supplies information about the existence and magnitude of the contact force to the user of the instrument.

As another example, U.S. Pat. No. 6,241,724, whose disclosure is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

Another example is presented in U.S. Pat. No. 6,915,149, whose disclosure is incorporated herein by reference. This patent describes a method for mapping a heart using a catheter having a tip electrode for measuring the local electrical activity. In order to avoid artifacts that may arise from poor tip contact with the tissue, the contact pressure between the tip and the tissue is measured using a pressure sensor to ensure stable contact.

U.S. Pat. No. 8,162,935, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 8,357,152, whose disclosure is incorporated herein by reference, describes systems and methods for measuring the contact pressure applied to a tip of a catheter using a magnetic field sensor in the tip and a magnetic field generator within the probe. The magnetic field sensor generates signals in response to the magnetic field generator within the probe, which are processed to determine the position of the tip relative to the position of the magnetic field generator, thereby indicating the amount of deformation of the tip and thus the pressure applied to the tip.

U.S. Pat. App. Pub. No. 2014/0187917, the entire disclosure of which is incorporated herein by reference, describes a catheter that carries a miniature transmitting coil and three sensing coils on opposing portions of a flexibly-jointed distal tip section. The transmitting coil is aligned with the longitudinal axis of the catheter and three sensing coils are also aligned with the longitudinal axis but positioned at an equal distance from the transmitting coil, and at equally-spaced radial positions about the longitudinal axis of the catheter. The miniature transmitting coil generates a magnetic field sensed by the three sensing coils which generate signals representative of axial displacement and angular deflection between the opposing portions of the distal tip section.

SUMMARY

Embodiments of the present invention are directed to catheter control systems that control the amount of power supplied to a catheter based on detected catheter tip contact force levels. By reducing or completely disabling the RF energy supplied to the catheter as the catheter is subjected to increasing levels of contact force, embodiments of the present invention reduce potential undesired damage to heart tissue due to excessive heating.

According to one embodiment of the present invention, a catheterization system includes: a catheter including an electrode and a sensor assembly configured to detect a contact force applied to the electrode; and a controller coupled to the catheter, the controller including a processor and memory storing instructions that, when executed by the processor, cause the processor to: receive a detected contact force from the sensor assembly of the catheter; control a power supplied to the electrode of the catheter to have a deactivated power level when the detected contact force is less than a first threshold contact force; control the power supplied to the electrode of the catheter to have a first power level when the detected contact force is greater than the first threshold contact force; and control the power supplied to the electrode of the catheter to have a deactivated power level when the detected contact force is greater than a cutoff contact force, the cutoff contact force being greater than the first threshold contact force.

The memory may further store instructions that, when executed by the processor, cause the processor to: control the power supplied to the electrode of the catheter to have a second power level when the detected contact force is greater than a second threshold contact force, the second threshold contact force being greater than the first threshold contact force and smaller than the cutoff contact force.

The memory may further store instructions that, when executed by the processor, cause the processor to: control the power supplied to the electrode of the catheter to have a zeroth power level when the detected contact force is less than the first threshold contact force and the detected contact force was previously greater than the first threshold contact force, the zeroth power level being greater than the first power level.

The memory may further store instructions that, when executed by the processor, cause the processor to: control the power supplied to the electrode of the catheter in accordance with a power control curve, the power control curve being a piecewise continuous function.

The memory may further store instructions that, when executed by the processor, cause the processor to: control the power supplied to the electrode along a first curve when the contact force is increasing; and control the power supplied to the electrode along a second curve different from the first curve when the contact force is decreasing.

The first threshold contact force may correspond to a noise threshold.

The detected contact force may include a smoothed contact force computed based on a plurality of contact force data from the sensor assembly.

The memory may further store instructions that, when executed by the processor, cause the processor to: compute the smoothed contact force by computing an average of the plurality of contact force data from the sensor assembly.

The memory may further stores instructions that, when executed by the processor, cause the processor to: compute the smoothed contact force by applying a Kalman filter to the plurality of the contact force data from the sensor assembly.

The memory may further store instructions that, when executed by the processor, cause the processor to: receive a user parameter; and adjust at least one of the first threshold contact force, the first power level, and the cutoff contact force in accordance with the user parameter.

According to one embodiment of the present invention, a method for controlling an ablation power applied to a catheter includes: receiving, by a controller including a processor and memory, a detected contact force from a sensor assembly of the catheter, the sensor assembly being configured to detect a contact force applied to the electrode; controlling, by the controller, a power supplied to an electrode of the catheter to have a deactivated power level when the detected contact force is less than a first threshold contact force; controlling, by the controller, the power supplied to the electrode of the catheter to have a first power level when the detected contact force is greater than the first threshold contact force; and controlling, by the controller, the power supplied to the electrode of the catheter to have a deactivated power level when the detected contact force is greater than a cutoff contact force, the cutoff contact force being greater than the first threshold contact force.

The method may further include: controlling the power supplied to the electrode of the catheter to have a second power level when the detected contact force is greater than a second threshold contact force, the second threshold contact force being greater than the first threshold contact force and smaller than the cutoff contact force.

The method may further include: controlling the power supplied to the electrode of the catheter to have a zeroth power level when the detected contact force is less than the first threshold contact force and the detected contact force was previously greater than the first threshold contact force, the zeroth power level being greater than the first power level.

The method may further include: controlling the power supplied to the electrode of the catheter in accordance with a power control curve, the power control curve being a piecewise continuous function.

The method may further include: controlling the power supplied to the electrode along a first curve when the contact force is increasing; and controlling the power supplied to the electrode along a second curve different from the first curve when the contact force is decreasing.

The first threshold contact force may correspond to a noise threshold.

The detected contact force may include a smoothed contact force computed based on a plurality of contact force data from the sensor assembly.

The method may further include: computing the smoothed contact force by computing an average of the plurality of contact force data from the sensor assembly.

The method may further include: computing the smoothed contact force by applying a Kalman filter to the plurality of contact force data from the sensor assembly.

The method may further include: receiving a user parameter; and adjusting at least one of the first threshold contact force, the first power level, and the cutoff contact force in accordance with the user parameter.

BRIEF DESCRIPTION OF THE DRAWINGS

These and other features and advantages of the present invention will be better understood by reference to the following detailed description when considered in conjunction with the accompanying drawings wherein:

FIGS. 5A-5E are graphs illustrating example power control curve according to various embodiments of the present invention.

DETAILED DESCRIPTION

The present invention is directed to a system and catheter for cardiac catheterization, where the catheter has a sensor assembly that provides signals representative of both position of the catheter and pressure exerted on a distal section of the catheter when it engages tissue and pressure exerted by the probe onto the tissue. The distal section of the catheter also includes an electrode for applying RF energy through the catheter to ablate the heart tissue at the site. Compared to conventional systems for cardiac catheterization, the control system controls the amount of RF energy (e.g., the amount of ablation power) applied to the electrode based on the amount of pressure (or contact force) applied to the distal section of the catheter. By reducing the amount of ablation power when the detected contact force increases, occurrences of excessive heating can be reduced or avoided, thereby reducing the risk of undesired damage to heart tissue. Similarly, in some embodiments of the present invention, a control system increases the amount of ablation power applied when the detected contact force decreases.

Figure 1A:
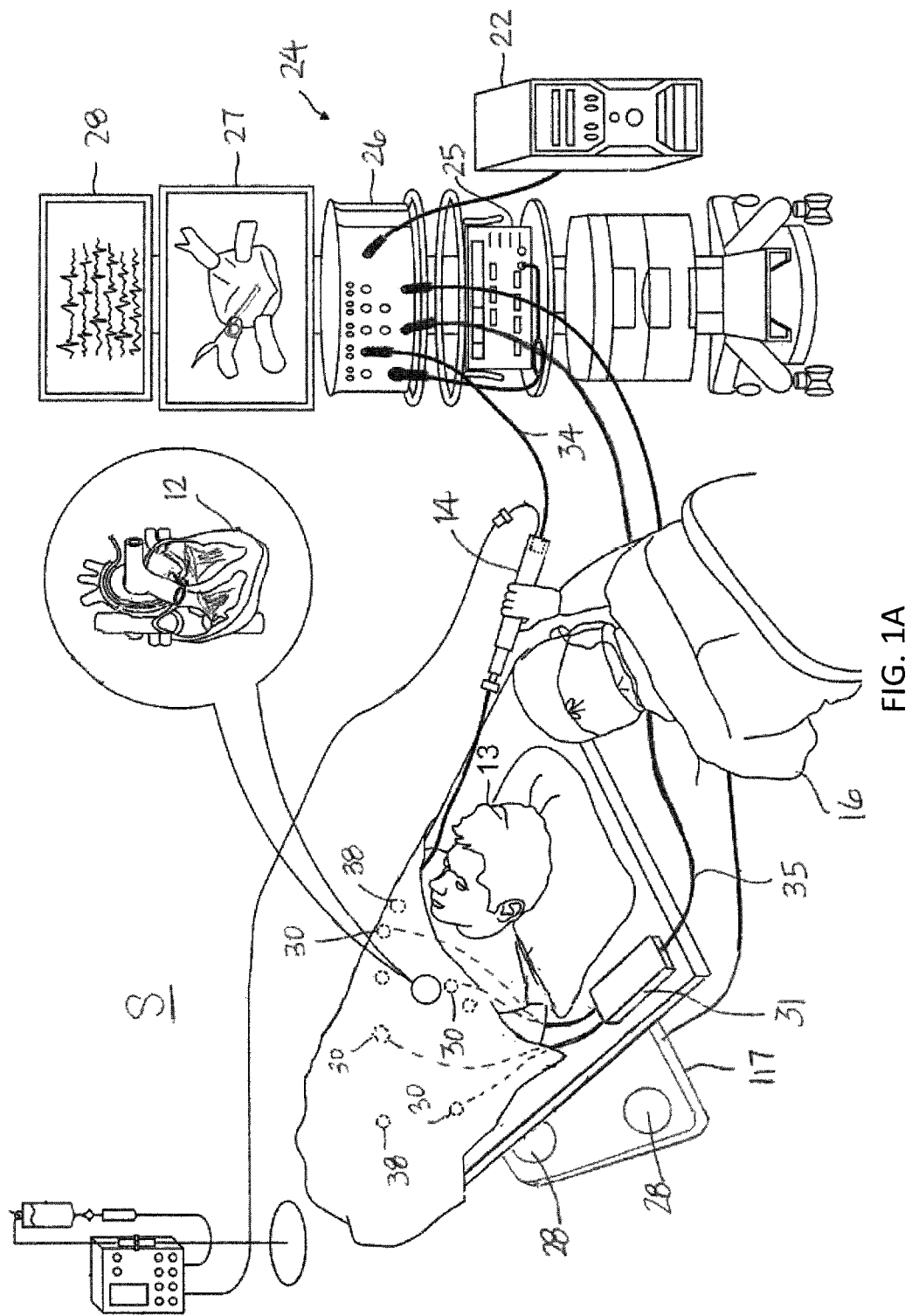
FIG. 1A is a schematic, pictorial illustration of a catheter-based medical system, in accordance with an embodiment of the present invention.

FIG. 1A is a pictorial illustration of a catheterization system S for performing exemplary catheterization procedures on a heart 12 of a living subject or patient 13, which is constructed and operative in accordance with a disclosed embodiment of the invention. The system comprises a catheter 14, which is percutaneously inserted by an electrophysiologist or operator 16 through the patient's vascular system into a chamber or vascular structure of the heart 12. The catheter 14 has a distal tip carrying one or more electrodes, and a control handle by which the operator 16 can manipulate to steer and deflect the catheter.

Electrical activation maps, anatomic positional information, i.e., of the distal portion of the catheter, and other functional images may then be prepared using a console 24, according to the methods disclosed in U.S. Pat. Nos. 6,226, 542, and 6,301,496, and in commonly assigned U.S. Pat. No. 6,892,091, whose entire disclosures are herein incorporated by reference. One commercial product embodying elements of the console 24 is the CARTO® 3 System, available from Biosense Webster, Inc., 3333 Diamond Canyon Road, Diamond Bar, Calif. 91765, which performs catheter localization and produces 3-D electroanatomic maps of the heart as required. These embodiments of the present invention may be modified by those skilled in the art to embody the principles of the invention described herein. For example, in some embodiments, these functions implemented by a radio frequency generator 25.

Areas determined to be abnormal, for example by evaluation of electrical activation maps, can be targeted and ablated by application of thermal energy, e.g., by passage of radiofrequency electrical current from a radiofrequency (RF) generator 25 of the console 24 through a cable 34 providing current to the catheter 14, including the ablation electrode 32 at the distal tip, which apply the radiofrequency energy to target tissue. The console 24 typically contains one or more ablation power generators 25, a patient interface unit (PIU) 26, and one or more displays 27 and 28 to display 3-D maps and electrograms. The catheter 14 is adapted to conduct ablative energy to the heart using radiofrequency energy. Such methods are disclosed in commonly assigned U.S. Pat. Nos. 6,814,733, 6,997,924, and 7,156,816, which are herein incorporated by reference. Ablation energy is conveyed from RF generator 25 to the heart 12 through the catheter electrodes via cable 34 which is connected to the console 24. Pacing signals and other control signals may also be conveyed from the console 24 through the cable 34 and the catheter electrodes to the heart 12. Moreover, electrical signals (for example, intracardiac electrocardiography or ECG signals) are conveyed from the heart 12 to the console 24 via the catheter electrodes.

In some embodiments of the system S, ECG body surface patches, including at least patches 30 are affixed to the patient's body. While the catheter electrodes are sensing intracardiac ECG signals, a plurality of electrodes in the ECG body surface patches 30 measure ECG signals across the heart and torso to provide reference signals for the intracardiac ECG signals measured by the catheter electrodes. However, embodiments of the present invention are not limited thereto and may be performed without the use of ECG body surface patches.

As part of the catheter localization capabilities of the console 24, according to one embodiment of the present invention, a magnetic field is generated around the patient 13, for example, by a location pad containing magnetic field generator coils 28 that is placed under the patient. The magnetic fields generated by coils 28 generate electrical signals in coils of an electromagnetic (EM) sensor located in the distal tip of catheter 14. The electrical signals are conveyed to the console 24 which includes a processor or "workstation" 22 that analyzes the signals so as to determine the coordinates of the position and orientation of catheter. However, embodiments of the present invention are not limited thereto and may be used in systems without localization capabilities.

As also part of the catheter localization capabilities of the console 24, the catheter electrodes are connected by lead wires (not shown) in the catheter and the cable 34 to current and voltage measurement circuitry in the console 24. The console 24 is also connected by wires and a patch unit 31 to a plurality of body surface electrodes 38, which may be any type of body electrodes known in the art, such as button electrodes, needle electrodes, subcutaneous probes, or patch electrodes. The body surface electrodes 38 are typically in galvanic contact with the body surface of the patient 13 and receive body surface currents therefrom. The body surface electrodes 38 may be adhesive skin patches generically referred to as active current location (ACL patches) and may be placed on the body surface of the patient 13 in the vicinity of the catheter 14. The console 24 includes voltage generators which are connected to the ACL patches 38 via wires 35 and which the processor 22 uses to calculate impedance of the patient tissue between the catheter electrodes and the location of the patches 38. Accordingly, the console 24 uses both magnetic-based position sensing and impedance-based measurements for catheter localization, as described in U.S. Pat. No. 7,536,218, issued to Govari et al., and U.S. Pat. No. 8,478,383, issued to Bar-Tal et al., the entire content of both of which are herein incorporated by reference.

As noted above, the catheter 14 is coupled (or connected) to the console 24, which enables the operator 16 to observe and regulate the functions of the catheter 14. The processor 22 and/or the console 24 include appropriate signal processing circuits coupled to drive a display 27 to display visual imagery including the 3-D electroanatomical maps.

Figure 1B:
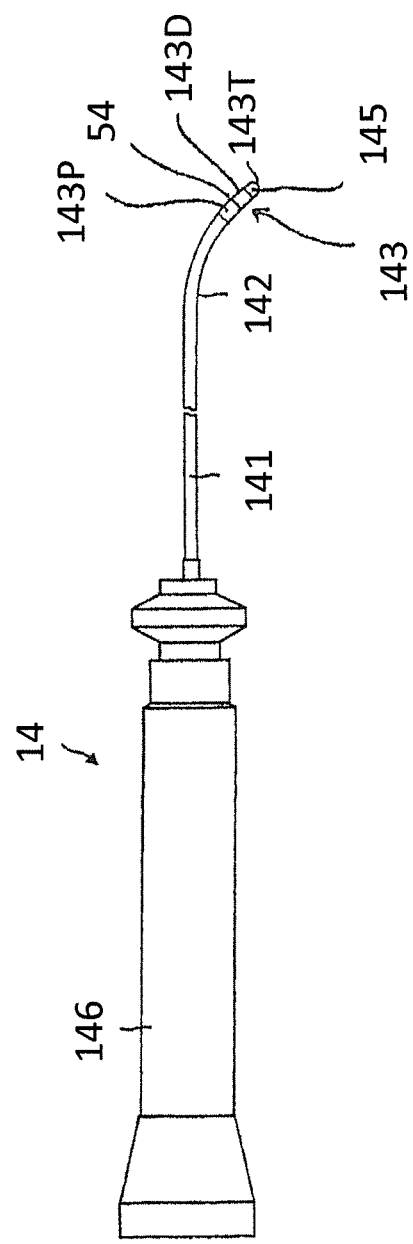
FIG. 1B is a side view of a catheter for use with the system of FIG. 1A, in accordance with an embodiment of the present invention.

As shown in FIG. 1B, the catheter 14 includes a control handle 146, an elongated catheter body 141, a deflectable intermediate section 142, and a distal section 143 having a proximal portion 143P, a distal portion 143D, and a distal tip end 143T. The distal section 143 carries at least a tip electrode 145 on its distal tip end 143T.

Figure 1C:
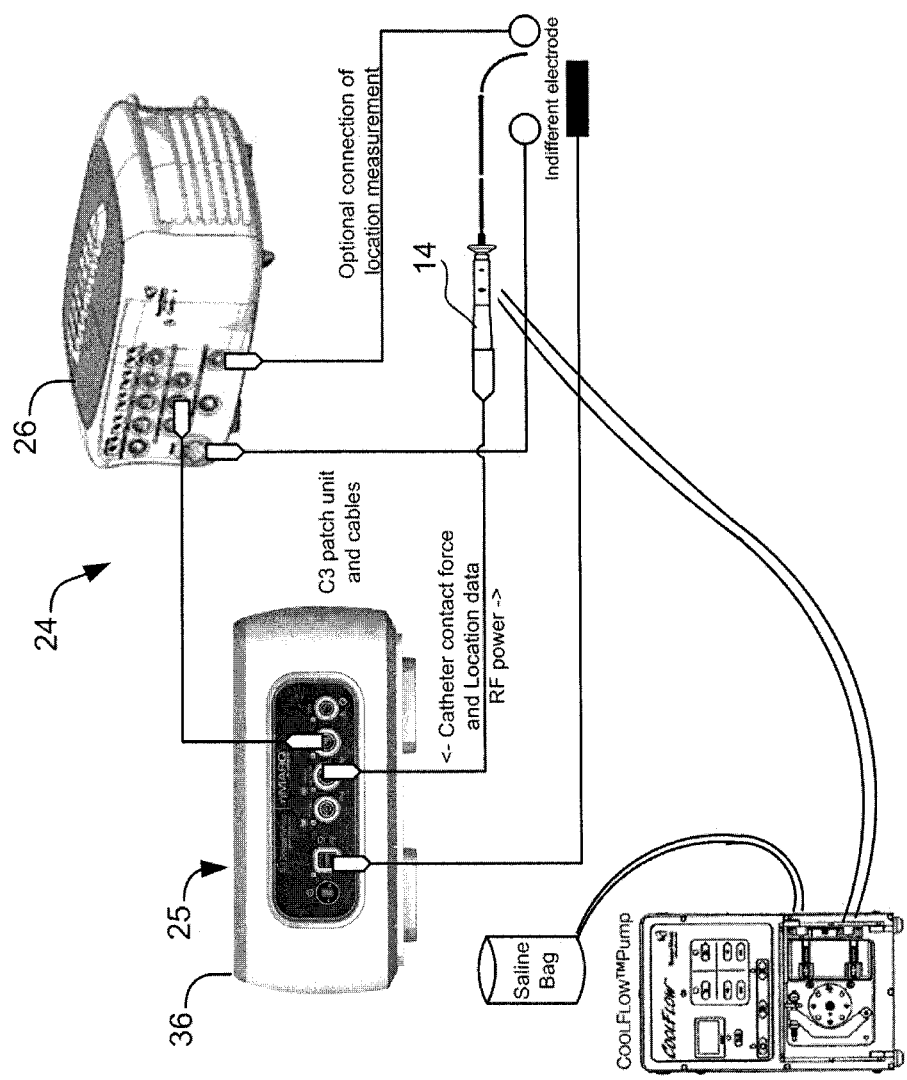
FIG. 1C is a schematic diagram illustrating components of the catheter-based medical system illustrated in FIG. 1A.
Figure 1D:
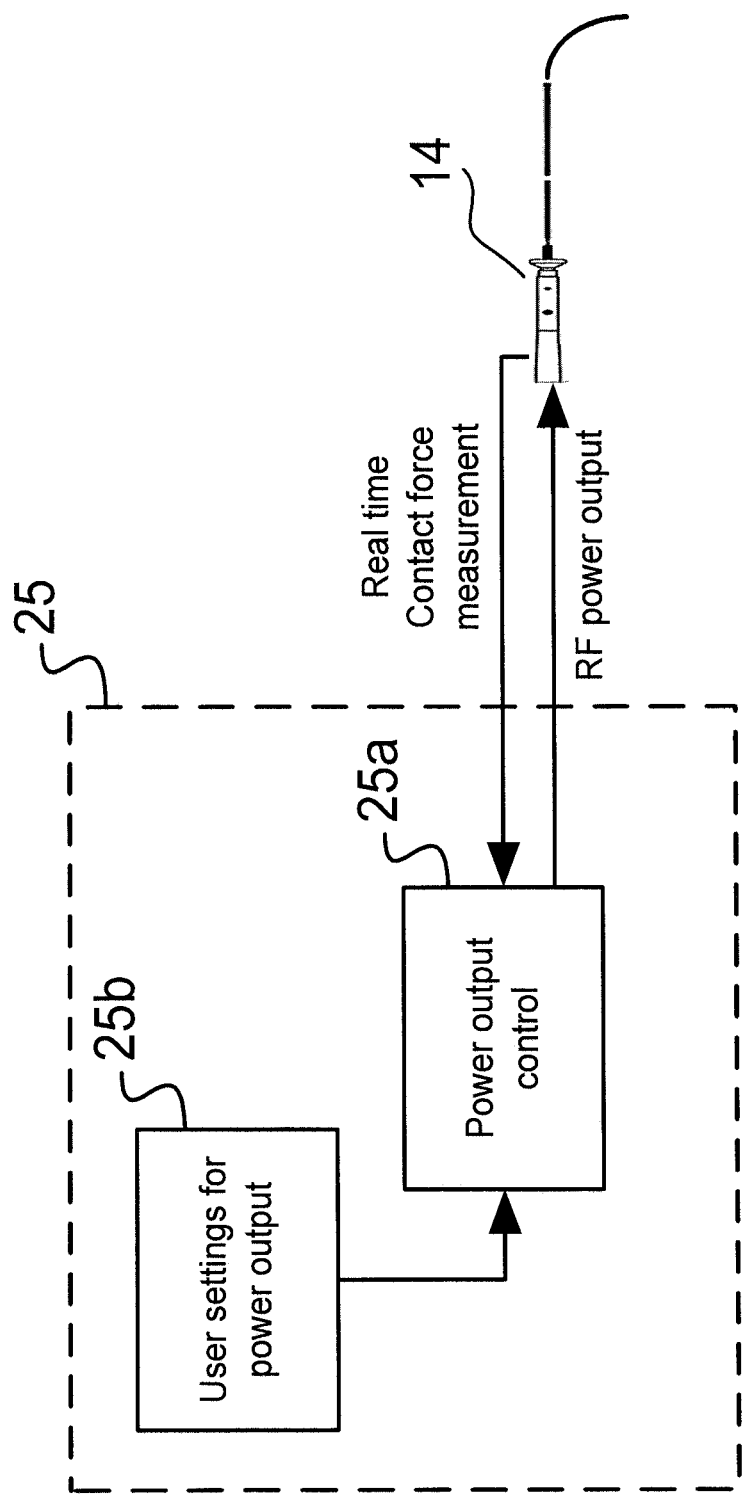
FIG. 1D is a schematic block diagram of a portion of the catheter-based medical system illustrated in FIG. 1A.

FIG. 1C is a schematic diagram illustrating components of the catheter-based medical system illustrated in FIG. 1A and FIG. 1D is a schematic block diagram illustrating the flow of information and power in a portion of the catheter-based medical system according to one embodiment of the present invention illustrated in FIG. 1A.

An operator 16, such as an electro-physiologist, inserts catheter 14 through the vascular system of a patient 13 so that a distal section 143 of the catheter enters a chamber of the patient's heart 12. The operator advances the catheter so that a distal tip 143T of the catheter engages endocardial tissue 70 at a desired location or locations. Catheter 14 is connected by a suitable connector at its proximal end to console 24. The console 24 may include an ablation power supply 25 such as a radio frequency or radiofrequency (RF) generator, which supplies high-frequency electrical energy via the catheter for ablating tissue in the heart at the locations engaged by the distal tip electrode 143T. Alternatively or additionally, the catheter and system may be configured to perform other therapeutic and diagnostic procedures that are known in the art.

Figure 2:
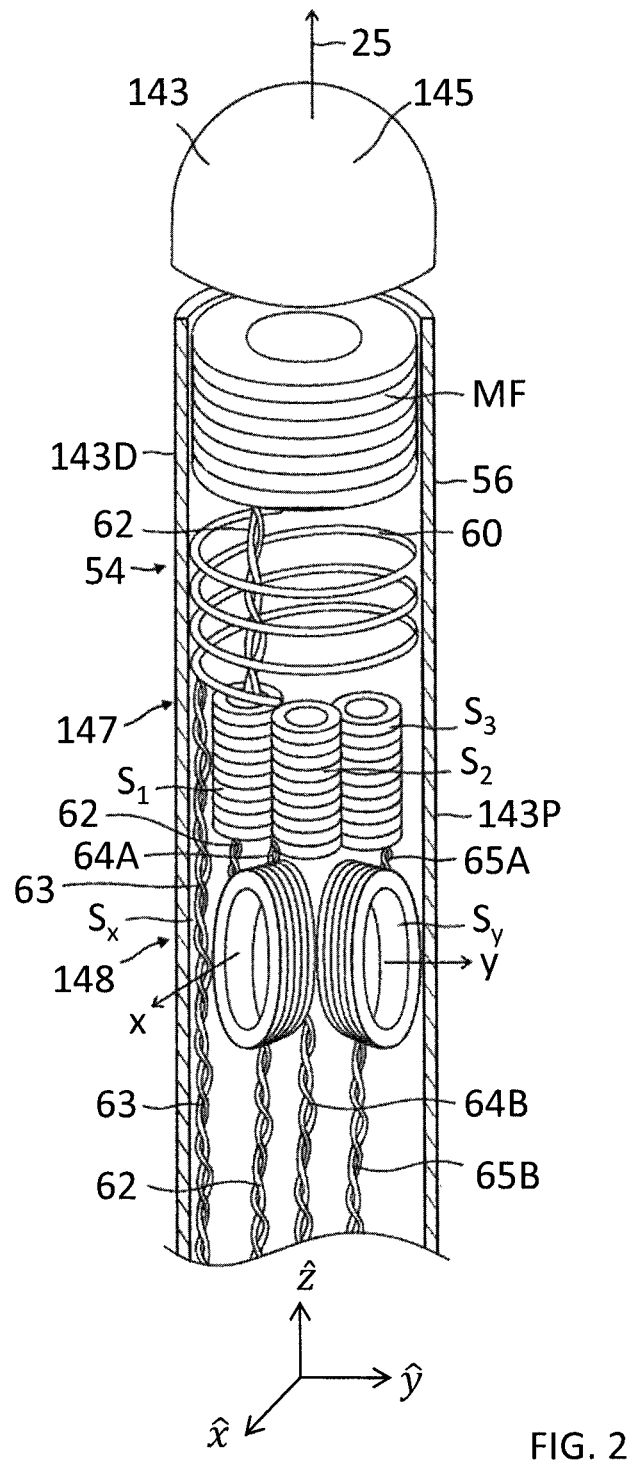
FIG. 2 is a schematic, cutaway view showing details of the distal section of the catheter of FIG. 1B.
Figure 3:
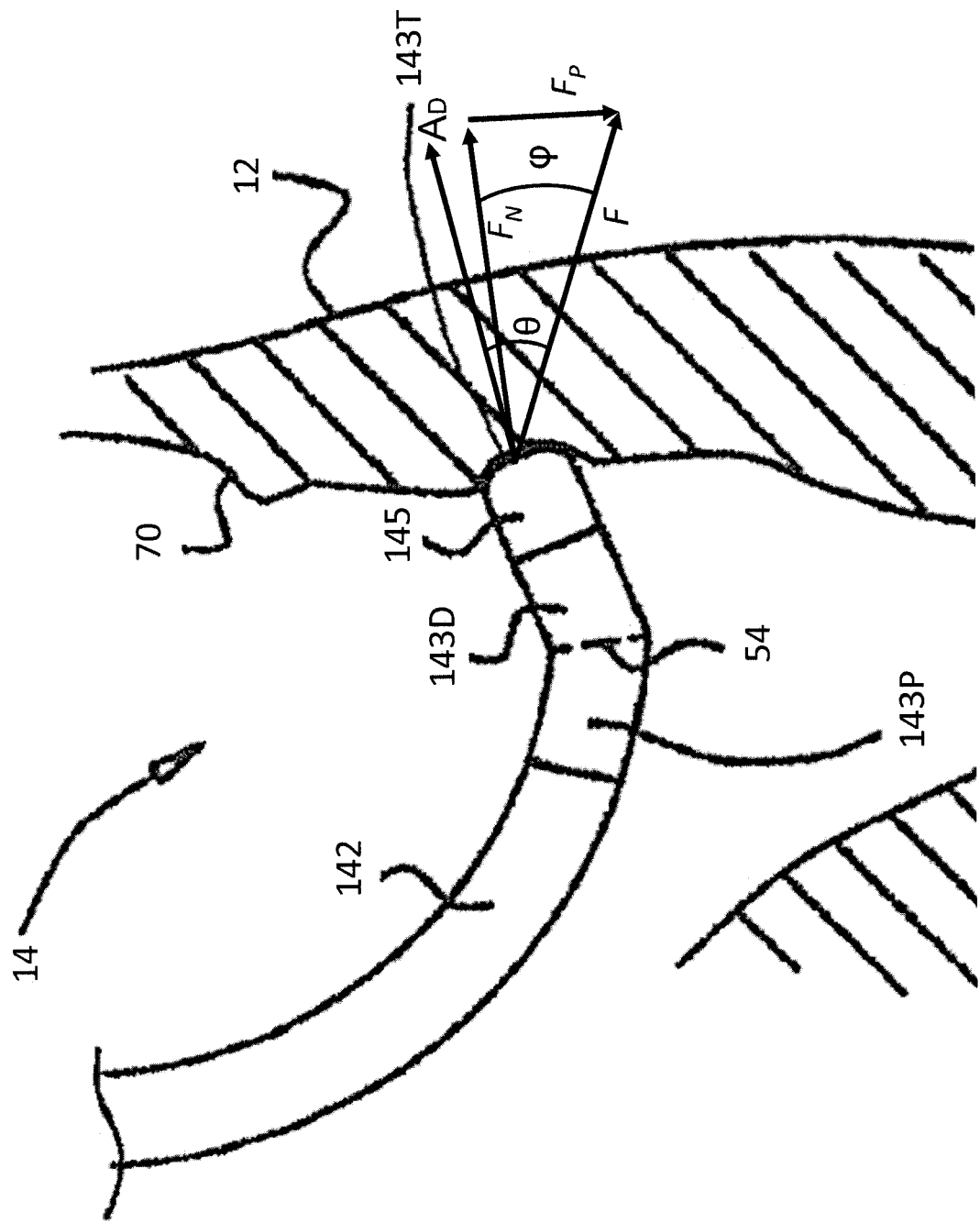
FIG. 3 is a schematic detail view showing the distal section of the catheter of FIG. 1B in contact with endocardial tissue.

FIG. 2 is a schematic, cutaway view showing details of the distal section of the catheter of FIG. 1B. FIG. 3 is a schematic detail view showing the distal section of the catheter of FIG. 1B in contact with endocardial tissue.

Console 24 or the ablation power supply 25 may use, in one embodiment, magnetic sensing to determine pressure and position data, including (i) axial displacement and angular deflection of the distal section 143 due to pressure from contact with endocardial tissue 70, and (ii) position coordinates of the distal section 143 within the heart 12. In one embodiment, the catheter 14 includes a sensor assembly for generating contact force data, including axial displacement and angular deflection of the distal section 143 of the catheter 14. According to one embodiment, the driver circuit 36 in console 24 drives a miniature magnetic field generator MF housed in a distal portion 143D of the distal section 143, as shown in FIG. 2. The field generator MF includes a coil whose axis is aligned with the Z axis coaxial with a longitudinal axis of the catheter. When the distal tip 143T of the catheter 14 contacts a surface and is deflected (e.g., as shown in FIG. 3), there is a change in the relative positions of the field generator MF with respect to a first sensor assembly 17, which includes sensor coils S1, S2, and S3. This, in turn, causes changes in the signals output by coils S1, S2, and S3, and the changes in signals are detected by the control console 24, thereby allowing the control console 24 to detect the amount of contact force experienced by the distal tip of the catheter 14. Systems and methods for detecting contact force data are described in more detail, for example, in U.S. Pat. No. 8,900,229, the entire disclosure of which is incorporated herein by reference. However, embodiments of the present invention are not limited to the embodiments described above and, instead, may be used with any appropriate method of detecting the amount of force applied to the catheter 14.

As noted above, in reference to FIG. 1D, the control console 24 includes an ablation power supply 25 such as an RF signal generator which supplies high frequency electrical energy via the catheter for ablating tissue in the heart 12 at the locations engaged by the distal tip section of the catheter. The control console 24 may also control the amount of RF energy (or power) it supplies to the catheter based on operator-provided power settings. However, embodiments of the present invention are not limited to RF signal generators and the ablation power supply may take the form of, for example, an ultrasound ablation power source, laser energy source, or cryo ablation energy source. The amount of energy delivered by the catheter to heart tissue can be controlled by a controller or power output controller 25a, which controls the power output to the catheter 14 (e.g., by controlling the output current of the ablation power supply). In addition, the power output controller 25a receives contact force measurements, in real time, in accordance with the contact force experienced by the distal tip 143T of the catheter 14. The power output controller 25a may include a processor and memory, where the memory stores instructions that, when executed by the processor, cause the processor to control the RF power output by the ablation power supply 25 (e.g., by adjusting the output current of the RF power output). The memory may also store settings 25b that are predetermined and/or are received from a user (e.g., set by the operator 16) via controls on the control console 24. The processor may be any sort of computing device suitable for controlling the power output, for example, a general purpose processor coupled to a memory (e.g., dynamic random access memory and/or flash memory), a microcontroller, an appropriately programmed field programmable gate array (FPGA), or an application specific integrated circuit (ASIC).

Figure 4:
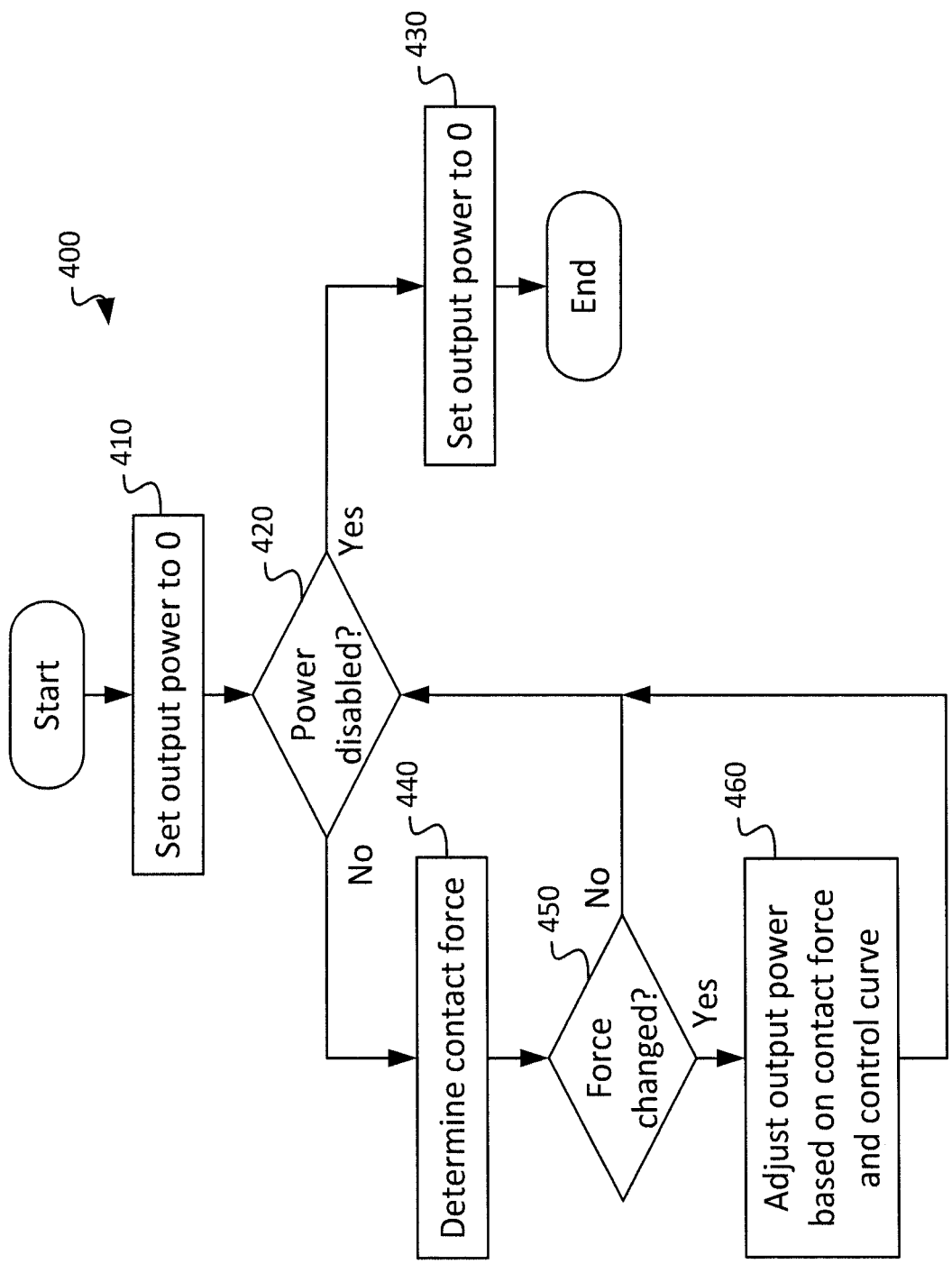
FIG. 4 is a flowchart illustrating a method for controlling a power supplied to a catheter according to one embodiment of the present invention.

FIG. 4 is a flowchart illustrating a method 400 according to one embodiment of the present invention for the power output controller 25a to control the power supplied to a catheter 14. As discussed above, the power output controller 25a may measure or receive a measured contact force experienced by the distal tip 143T of the catheter 14, as detected by changes in the magnetic fields detected by sensor coils S1, S2, and S3, although embodiments of the present invention are not limited thereto and other techniques may be used to measure the forces exerted on the distal tip 143T of the catheter 14.

Referring to FIG. 4, in operation 410, after the operator has activated the power on the catheter, the power output controller 25a may initially set the output power to 0 (or a deactivated power level) so that no power is applied until the catheter 14 comes into contact with tissue (however, embodiments of the present invention are not limited thereto and, in some embodiments, ablation power is applied to the catheter 14 before contact with tissue). In operation 420, the power output controller 25a determines whether the operator 16 has manually disabled power output. If so, then the process proceeds to operation 430, in which case the output power is set to 0 (or a deactivated power level) and the process ends. If the operator 16 has not disabled the power, then, in operation 440, the power output controller 25a determines the contact force applied to the distal tip 143T of the catheter 14 based on contact force data from the catheter 14 by, for example, receiving a calculated measurement from the patient interface unit 26 or by calculating a force based on received magnetic field strength data from the sensor coils (e.g., coils S1, S2, and S3). In operation 450, the power output controller 25a determines, from the contact force data, if the contact force has changed in comparison to the previously detected contact force. If not, then the power output controller 25a cycles back to operation 420. If the contact force has changed, then, in operation 460, the power output controller 25a adjusts the output power based on the contact force determined in operation 440 and a control curve, as described below. After adjusting the output power, the power output controller 25a returns to operation 420.

The contact force applied to the heart wall is a vector containing a component normal (or perpendicular) to the surface of the tissue (e.g., the heart wall) and components along directions parallel to the surface of the tissue. The contact force may be denoted as CF(F, θ, t), where F is the magnitude of the contact force, θ is the angle of the force vector from the axis $A_P$ that extends along the distal section 143D (see FIG. 1B) of the catheter, and t is time (e.g., the time at which the force was measured). In some embodiments of the present invention, the magnitude of the force F is used to provide power feedback control. In other embodiments of the present invention, the normal component $F_N$ of the force will be used to provide power feedback control. The normal component $F_N$ of the force is the projection of the force vector on the axis that is orthogonal to the heart tissue that the tip 143T is in contact with. The power output controller 25a calculates the projection of the force on the normal axis to the heart tissue surface, using the orientation of the catheter and an approximation of the orientation of the surface in contact, based on the 3-D structure and catheter location information provided by the console 24.

At certain angles φ between the catheter distal tip 143T and the heart tissue surface, the parallel force $F_P$ applied along a direction tangential to the heart wall may cause the catheter to slip and move away from its intended target. This may occur when $(F_P\equiv)F(t)\cdot\cos[\varphi(t)]>\mu\cdot(F_N\equiv)\cos[\varphi(t)]\cdot F(t)$, where μ approximates a coefficient of friction (or equivalent thereof) of the catheter tip on the heart wall, although μ may vary considerably from place to place on the heart wall.

According to one embodiment of the present invention, the power level is controlled based on the force applied along the direction normal $F_N$ to the tissue as well as based on access to the tissue and the specific anatomy. For example, an isthmus line may be performed with relatively low normal force to the tissue compared to the force applied in ablation around the septum of the right atrium. Therefore, the force threshold parameters and power levels applied may be varied based on the type of procedure performed and may be controlled by the operator 16.

Figure 5A:
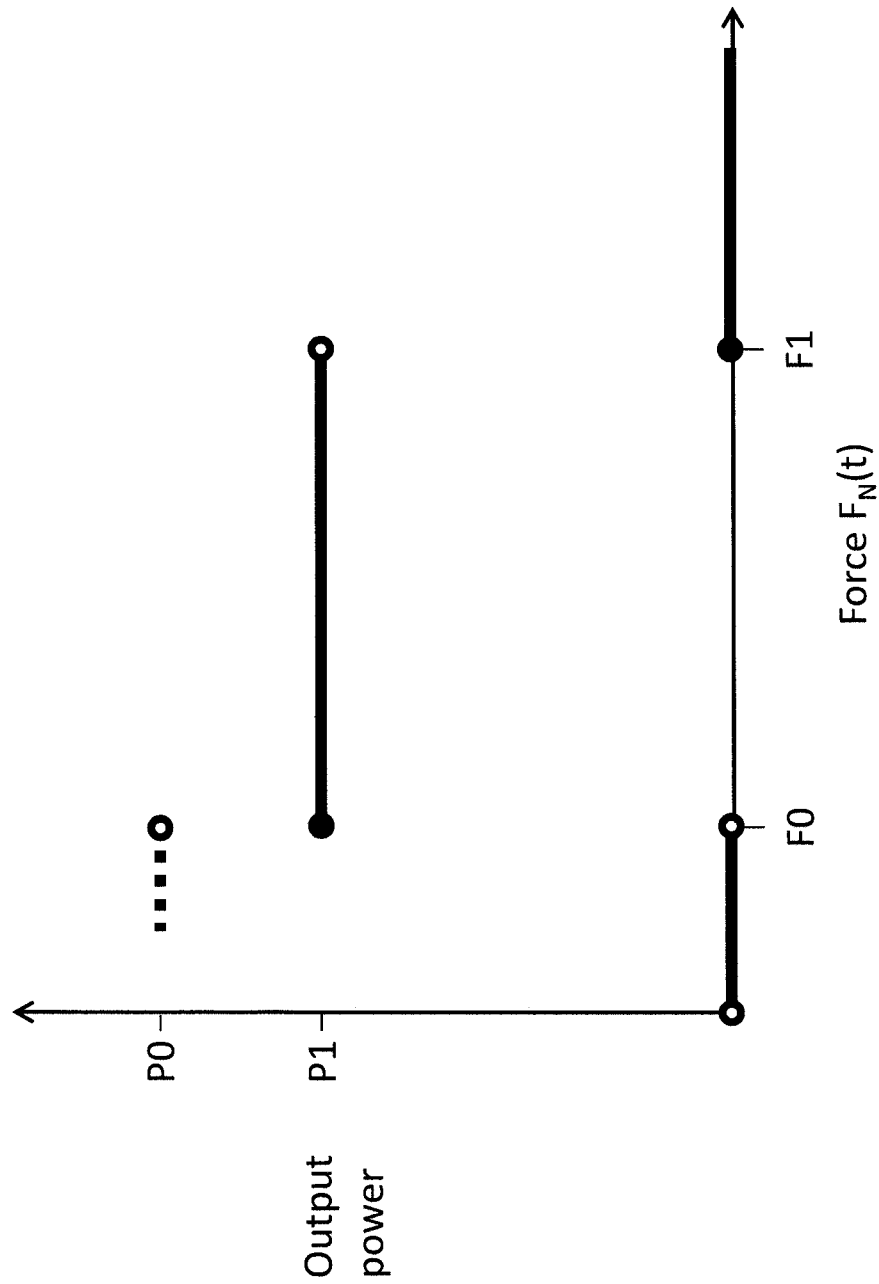

FIG. 5A is a graph illustrating a control curve or power control curve according to one embodiment of the present invention. According to one embodiment of the present invention, as shown in FIG. 5A, when contact is detected (based on, e.g., a detected contact force $F_N(t)$ on the catheter exceeds a zeroth threshold force F0 or temperature response to ablation), then the power at the catheter may be turned on at a first level P1. If more force is applied to the catheter, thereby increasing the detected contact force, so that the force exceeds a first threshold force F1 (or a cutoff contact force Fmax), then the power delivered to the catheter is turned off (or set to a deactivated power level) so as to reduce the likelihood of creating steam pops or overheating of the heart tissue. Conversely, if the catheter is withdrawn from the heart wall (or the heart moves away from the catheter) and the detected contact force on the catheter tip drops below F0, then the power is decreased to a zeroth power level P0 so that, the power delivered to the tissue can remain relatively stable. This control curve is summarized below:

$$P_{out}(t) = \begin{cases} 0 & F_N(t) < F0, \text{ before initial contact} \\ P0 & F_N(t) < F0, \text{ after initial contact} \\ P1 & F0 < F_N(t) < F1 \\ 0 & F1 < F_N(t) \end{cases}$$

where F1 is Fmax. In some embodiments, P0 may be 0.

In some embodiments of the present invention such as the example given above, the output power applied at a given force is direction or sequence sensitive (or "path dependent"). In the above example, the output power when $F_N(t)<F0$ differs depending on whether or not the contact force $F_N(t)$ has exceeded the zeroth threshold F0 yet. As another example, the output power may be sequence sensitive so that the catheter does not turn on again after the operator 16 withdraws the catheter after intentionally pushing and holding the catheter forcefully (or hard) into the tissue. In some embodiments, the power control curve may intentionally have hysteresis, where, for example, increasing contact force quickly decreases power output, while subsequent decrease of contact force more slowly increases power output. As still another example, the rate at which the output power level increases or decreases may be controlled by the rate at which the contact force changes (e.g., based on the first derivative of the contact force). As such, the power delivered to the tissue may differ based on whether the contact force is increasing or decreasing or based on whether or not the catheter has made contact with tissue.

In some embodiment of the present invention, the power control curve may have other shapes that are continuous or piecewise continuous functions of force. For example, a more complex power control curve is shown below:

$$P_{out}(t) = \begin{cases} 0 & F_N(t) < F0, \text{ before initial contact} \\ P0 & F_N(t) < F0, \text{ after initial contact} \\ P1 & F0 < F_N(t) < F1 \\ P2 & F1 < F_N(t) < F2 \\ P3 & F2 < F_N(t) < F3 \\ 0 & F3 < F_N(t) \end{cases}$$

where F3 is Fmax.

Figure 5B:
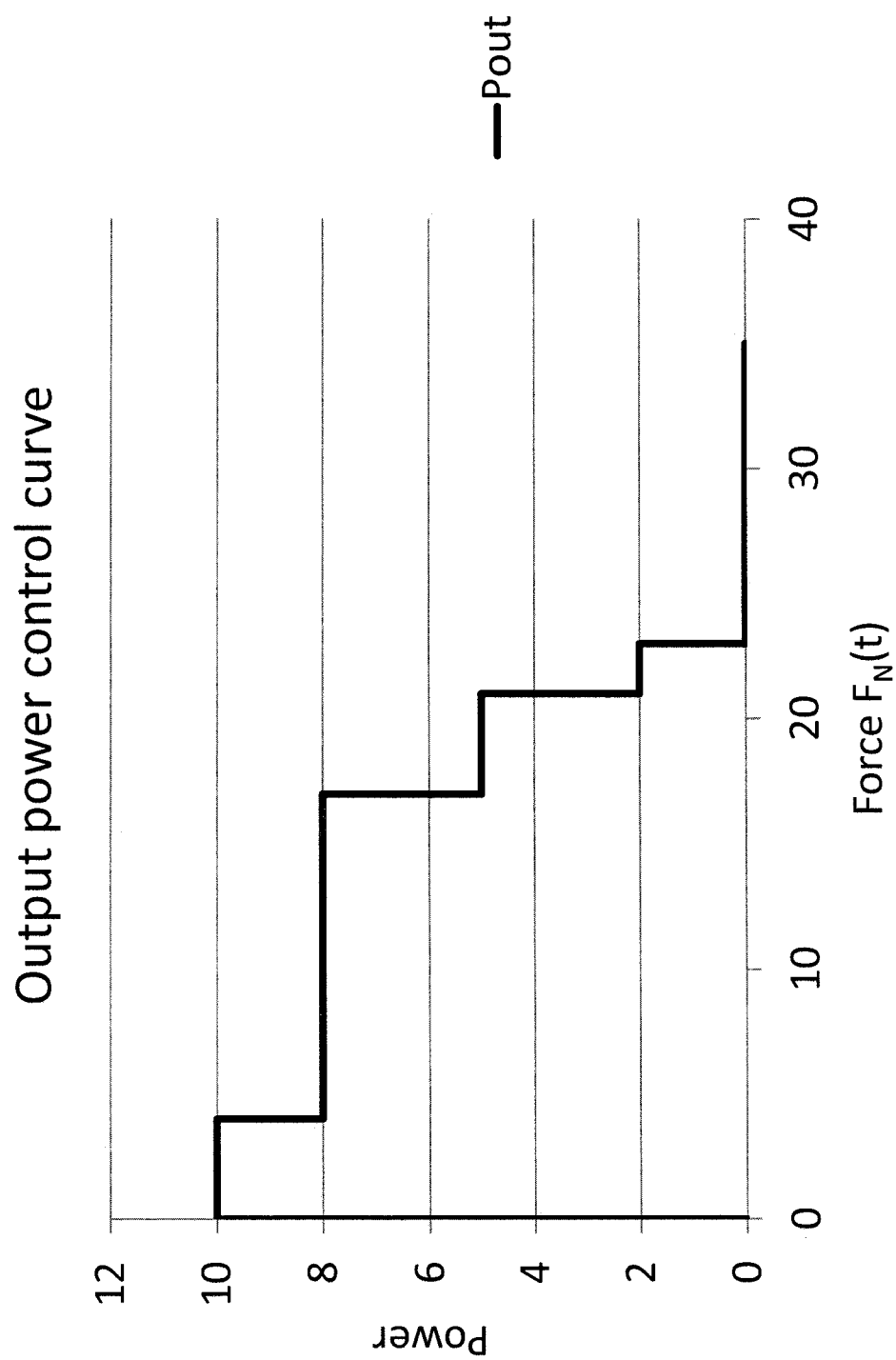

FIG. 5B is a graph illustrating a power control curve according to another embodiment of the present invention. As seen in FIG. 5B, in one embodiment, output power may be initially applied at a highest value as soon as the catheter detects contact (e.g., a contact force $F_N(t)$ greater than a noise threshold) and decreases the power applied in steps as the contact force $F_N(t)$ increases.

Figure 5D:
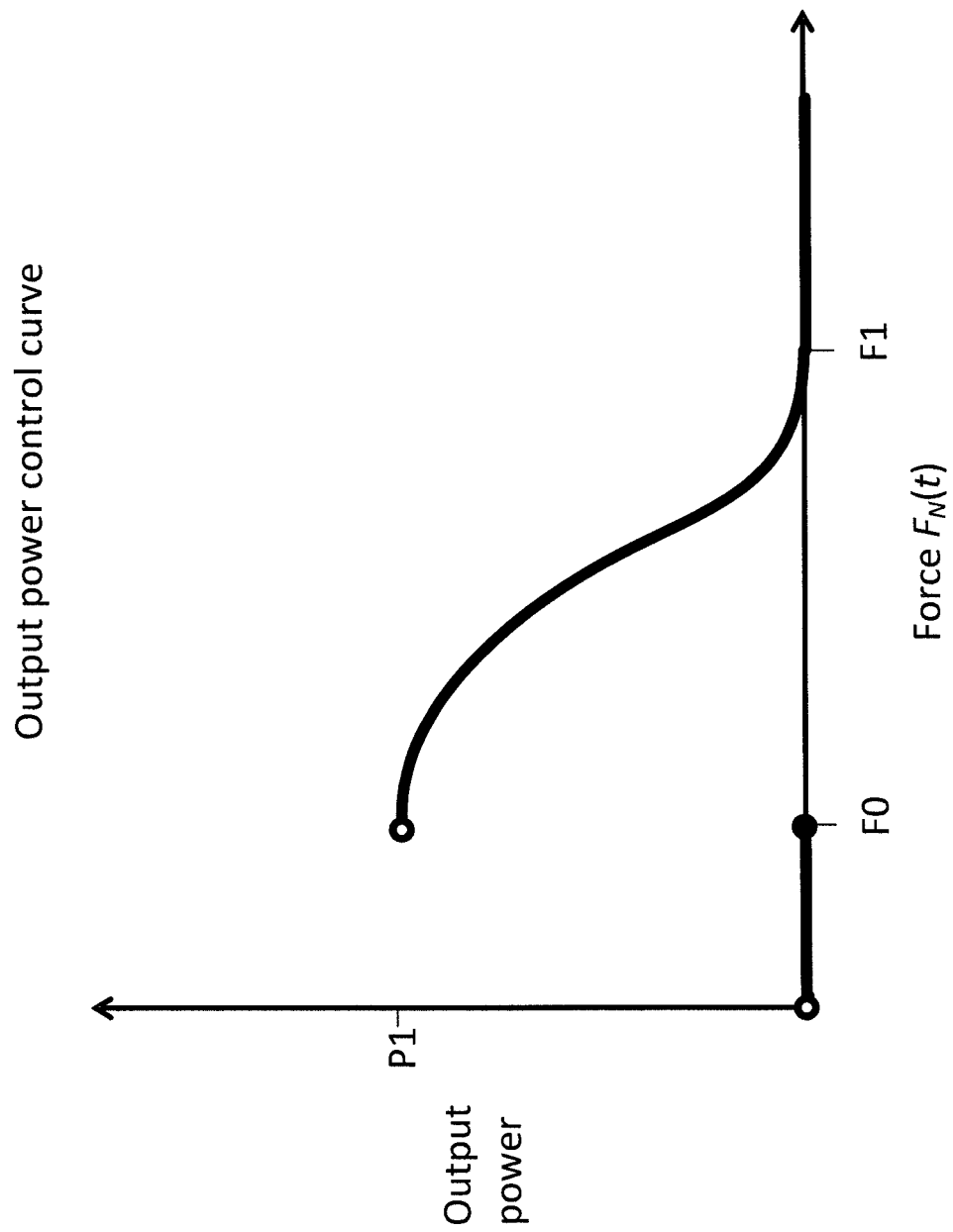
Figure 5E:
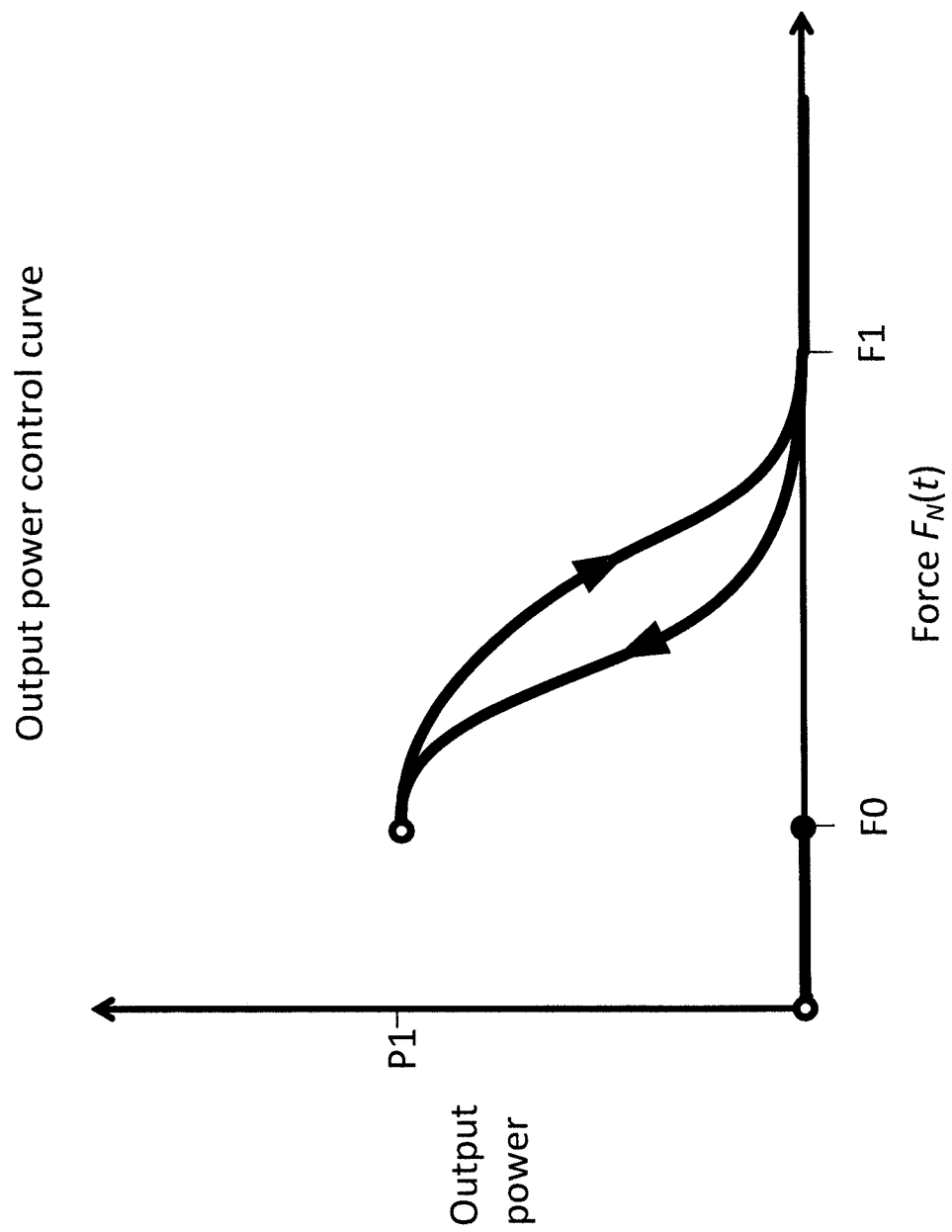

While the control curves depicted in FIG. 5A-5B are step functions, embodiments of the present invention are not limited thereto. Output power control curves of some embodiments of the present invention generally decrease output power level with increasing contact force, although zero power or low power may initially be applied at lower levels of force (e.g., forces below F0 in FIG. 5A) until an initial threshold contact force (e.g., F0 in FIG. 5A) is detected. For example, the output power control curve may decrease the power linearly from a zeroth power level P0 at a threshold contact force F0 until a power level of 0 at a cutoff contact force Fmax (here, F1), as shown in FIG. 5C. As still another example, the output power control curve may decrease the power along smooth, continuous sigmoidal (or "S") curve, as shown in FIG. 5D. FIG. 5E is an example of a power control curve exhibiting hysteresis.

As discussed above, the particular power levels (P0, P1, etc.) and contact force thresholds (F0, F1, etc.) may be adjusted by parameters set by a user such as the operator 16 based on the particular needs or circumstances. As such, the same power control curve may be used in multiple circumstances, with the particular values of the various output power levels and contact force thresholds adjusted or scaled based on those user parameters. Similarly, in circumstances where the power levels are controlled in accordance with mathematical functions, various constants (such as coefficients) in those mathematical functions may be adjusted by the user based on the circumstances.

Figure 6A:
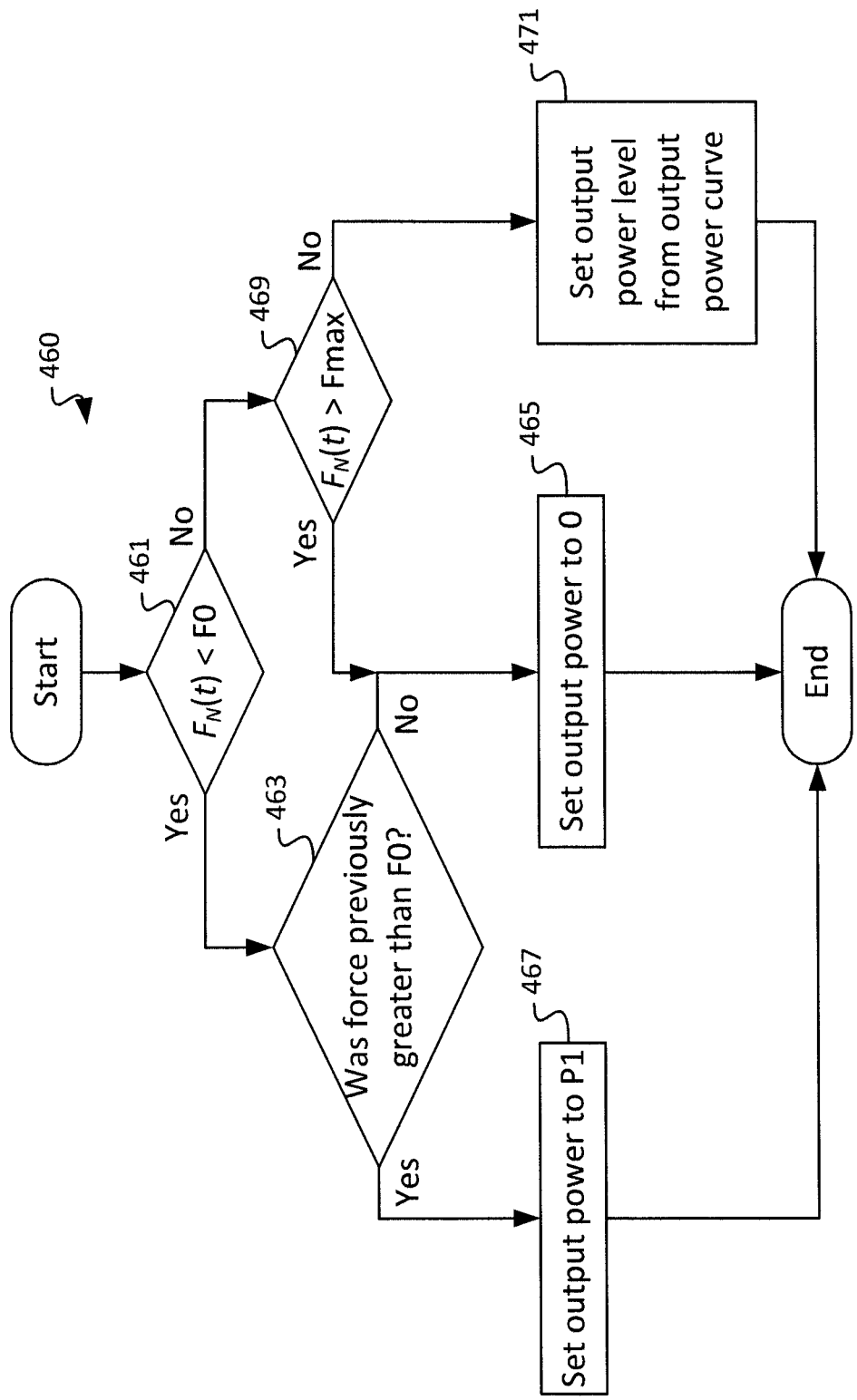
FIG. 6A is a flowchart illustrating a method for adjusting the output power based on the contact force and the control curve according to one embodiment of the present invention.

The output power control curves may be implemented in the memory of the controller in any of a number of ways, such as a lookup table mapping a contact force to an output power, a function call, and a state machine, FIG. 6A is a flowchart illustrating a method 460 for adjusting the output power based on the contact force and the control curve according to one embodiment of the present invention. In operation 461, the processor of the power output controller 25a determines whether the measured force is less than a threshold force (F0). If so, then, in operation 463, the processor determines whether the force $F_N(t)$ was previously greater than F0 (e.g., whether this is before or after "initial contact"). If not, than the output power is set to 0 in operation 465. If so, then the output power is set to P1 in operation 467. If the measured force was determined to not be less than F0 in operation 461, then, in operation 469, the processor determines whether the measured force $F_N(t)$ is greater than a cutoff contact force (Fmax). If so, then the processor sets the output power to zero in operation 465. If not, then the processor sets the output power based on the output power curve. For example, in a stepwise output power curve, the processor may determine which contact force range the currently measured contact force $F_N(t)$ falls into and output power at the corresponding level. As another example, the measured contact force $F_N(t)$ may be supplied to a mathematical function (e.g., a polynomial, exponential, or sigmoidal function) that maps the force to a corresponding output power. As still another example, as described above, the output power curve may exhibit hysteresis and the output power may depend on other factors such as whether the contact force is increasing or decreasing, or the rate at which the power is increasing or decreasing.

The position of the heart tissue varies over time due to the beating of the heart tissue as well as other motion within the body such as the breathing of the patient 13. As a result, the force applied to the heart wall by the catheter tip varies over time (hence, the force $F_N(t)$ is expressed as a function over time). Because the motion and the concomitant change in force can be relatively fast compared to the ablation time for the catheter, embodiments of the present invention are also directed to mitigating or eliminating these temporal effects.

According to one embodiment of the present invention, the measured contact force CF(F, θ, t) is smoothed by the power output controller 25a (or other signal processing device) over a period (or integration time $T_{int}$) longer than the instantaneous heart rate or to track the effect through a period longer than the ablation period to generate the smoothed contact force SCF(t). The normal component $SF_N(t)$ of the smoothed contact force may be computed by SCF(t)·Cos[φ], noting that φ may also vary over time.

Figure 6B:
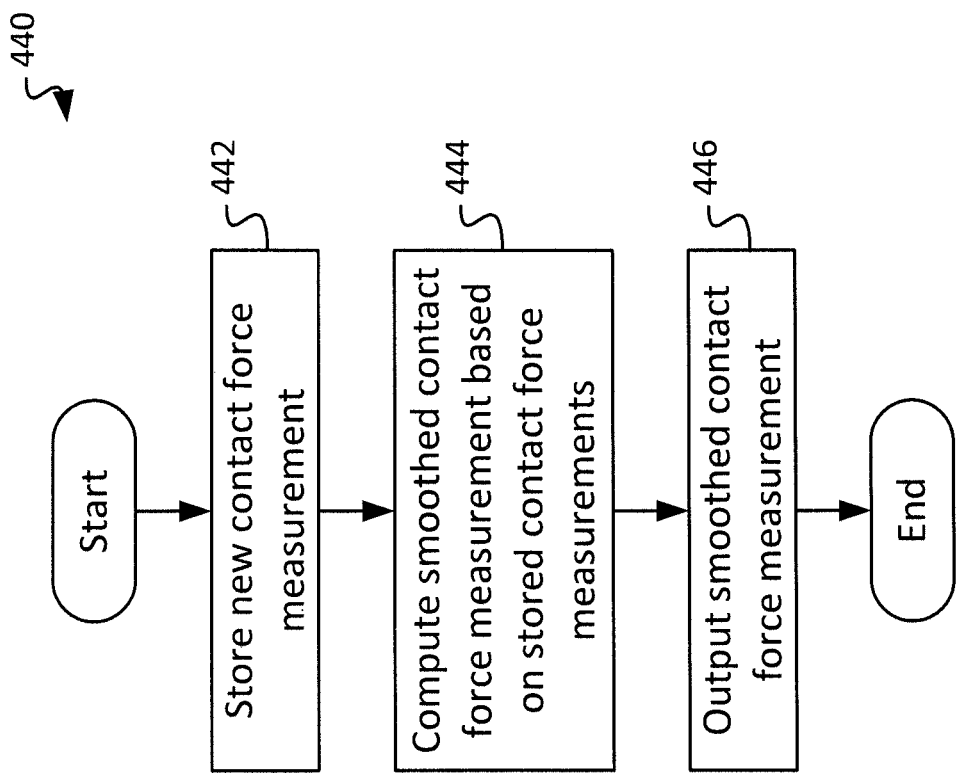
FIG. 6B is a flowchart illustrating a method for calculating a smoothed contact force according to one embodiment of the present invention.

FIG. 6B is a flowchart illustrating a method 440 for adjusting the output power based on a smoothed contact force and the control curve according to one embodiment of the present invention. In operation 442, the new contact force measurement is stored in memory, such as the memory of the power output controller 25a. In operation 444, the processor of the power output controller 25a computes the smoothed contact force SCF(t). The smoothing may be performed by averaging the values at times $T_s$ over the period (e.g., calculating a moving average) or using a statistical estimation technique such as a Kalman filter and the processor outputs the smoothed contact force SCF(t) to, for example, operation 450 to determine if the smoothed force has changed.

As such, an output power control curve may define a relationship between an output power $P_{out}(t)$ in accordance with a smoothed contact force $SF_N(t)$ as follows:

$$P_{out}(t) = \begin{cases} P1 & SF_N(t) < SF_N 1 \\ P2 & SF_N 1 < SF_N(t) < SF1_N 2 \\ P3 & SF_N 2 < SF_N(t) \end{cases}$$

where $SF_N 1$ and $SF_N 2$ are parameters to the system that represent the desired contact force operation range (e.g., user defined parameters that may be set based on the type of procedure and the portion of the heart in which the ablation is to be performed). In this example, $SF_N 2$ corresponds to the cutoff contact force Fmax.

Similarly, P1, P2, and P3 are also parameters that indicate three different reference levels of power to be supplied, where P1 is the power applied in a low contact situation (e.g., a smoothed contact force less than $SF_N 1$), P2 is the power applied in an operating range (e.g., a smoothed contact force greater than $SF_N 1$ and less than $SF_N 2$), and P3 is the power applied in a high contact situation (e.g., a smoothed contact force greater than $SF_N 2$).

In addition, in some embodiments of the present invention, the power is gradually changed around the threshold levels of contact force, rather than using step functions.

In addition, in some embodiments of the present invention, the power output is moderated as a function of contact surface area (e.g., a function of contact force, catheter geometry, and impedance).

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheterization system comprising:
   a catheter comprising an electrode and a sensor assembly configured to detect a force applied to the electrode by a surface of a tissue; and
   a controller coupled to the catheter, the controller comprising a processor and memory storing instructions that, when executed by the processor, cause the processor to:
   receive a force vector from the sensor assembly of the catheter;
   compute a detected normal component of a contact force corresponding to a component of the force vector along a direction normal to the surface of the tissue;
   control a power supplied to the electrode of the catheter to have a deactivated power level when the detected normal component of the contact force is less than a first threshold contact force;
   control the power supplied to the electrode along a first curve when the detected normal component of the contact force is increasing;
   control the power supplied to the electrode along a second curve different from the first curve when the detected normal component of the contact force is decreasing;
   control the power supplied to the electrode of the catheter to have a first power level along the first curve based on detecting a change in the detected normal component of the contact force from smaller than the first threshold contact force to greater than the first threshold contact force; and
   control the power supplied to the electrode of the catheter to have a deactivated power level along the first curve based on detecting a change in the detected normal component of the contact force from smaller than a cutoff contact force to greater than the cutoff contact force, the cutoff contact force being greater than the first threshold contact force.

2. The catheterization system of claim 1, wherein the memory further stores instructions that, when executed by the processor, cause the processor to:
control the power supplied to the electrode of the catheter to have a second power level when the detected normal component of the contact force is greater than a second threshold contact force, the second threshold contact force being greater than the first threshold contact force and smaller than the cutoff contact force; and
control the first power level to be constant while the detected normal component of the contact force is greater than the first threshold and smaller than the second threshold contact force.

3. The catheterization system of claim 1, wherein the memory further stores instructions that, when executed by the processor, cause the processor to:
control the power supplied to the electrode of the catheter to have a zeroth power level along the second curve based on detecting a change in the detected normal component of the contact force from greater than the first threshold contact force to less than the first threshold contact force, the zeroth power level being greater than the first power level.

4. The catheterization system of claim 1, wherein the memory further stores instructions that, when executed by the processor, cause the processor to:
control the power supplied to the electrode of the catheter in accordance with a power control curve, the power control curve being a piecewise continuous function comprising the first curve and the second curve.

5. The catheterization system of claim 1, wherein the first threshold contact force corresponds to a noise threshold.

6. The catheterization system of claim 1, wherein the detected normal component of the contact force comprises a smoothed contact force computed based on a plurality of contact force data from the sensor assembly.

7. The catheterization system of claim 6, wherein the memory further stores instructions that, when executed by the processor, cause the processor to:
compute the smoothed contact force by computing an average of the plurality of contact force data from the sensor assembly.

8. The catheterization system of claim 6, wherein the memory further stores instructions that, when executed by the processor, cause the processor to:
compute the smoothed contact force by applying a Kalman filter to the plurality of the contact force data from the sensor assembly.

9. The catheterization system of claim 1, wherein the memory further stores instructions that, when executed by the processor, cause the processor to:
receive a user parameter; and
adjust at least one of the first threshold contact force, the first power level, and the cutoff contact force in accordance with the user parameter.

10. A method for controlling an ablation power applied to a catheter, the method comprising:
receiving, by a controller comprising a processor and memory, a force vector from a sensor assembly of the catheter, the sensor assembly being configured to detect a force applied to an electrode of the catheter by a surface of a tissue;
computing, by the controller, a detected normal component of a contact force corresponding to a component of the force vector along a direction normal to the surface of the tissue;
controlling, by the controller, a power supplied to an electrode of the catheter to have a deactivated power level when the detected normal component of the contact force is less than a first threshold contact force;
controlling, by the controller, the power supplied to the electrode along a first curve when the detected normal component of the contact force is increasing;
controlling, by the controller, the power supplied to the electrode along a second curve different from the first curve when the detected normal component of the contact force is decreasing;
controlling, by the controller, the power supplied to the electrode of the catheter to have a first power level along the first curve based on detecting a change in the detected normal component of the contact force from smaller than the first threshold contact force to greater than the first threshold contact force; and
controlling, by the controller, the power supplied to the electrode of the catheter to have a deactivated power level along the first curve based on detecting a change in the detected normal component of the contact force from smaller than a cutoff contact force to greater than the cutoff contact force, the cutoff contact force being greater than the first threshold contact force.

11. The method of claim 10, further comprising:
controlling the power supplied to the electrode of the catheter to have a second power level when the detected normal component of the contact force is greater than a second threshold contact force, the second threshold contact force being greater than the first threshold contact force and smaller than the cutoff contact force; and
controlling the first power level to be constant while the detected normal component of the contact force is greater than the first threshold and smaller than the second threshold contact force.

12. The method of claim 10, further comprising:
controlling the power supplied to the electrode of the catheter to have a zeroth power level along the second curve based on detecting a change in the detected normal component of the contact force from greater than the first threshold contact force to less than the first threshold contact force, the zeroth power level being greater than the first power level.

13. The method of claim 10, further comprising: controlling the power supplied to the electrode of the catheter in accordance with a power control curve, the power control curve being a piecewise continuous function comprising the first curve and the second curve.

14. The method of claim 10, wherein the first threshold contact force corresponds to a noise threshold.

15. The method of claim 10, wherein the detected normal component of the contact force comprises a smoothed contact force computed based on a plurality of contact force data from the sensor assembly.

16. The method of claim 15, further comprising: computing the smoothed contact force by computing an average of the plurality of contact force data from the sensor assembly.

17. The method of claim 15, further comprising: computing the smoothed contact force by applying a Kalman filter to the plurality of contact force data from the sensor assembly.

18. The method of claim 10, further comprising:
receiving a user parameter; and
adjusting at least one of the first threshold contact force, the first power level, and the cutoff contact force in accordance with the user parameter.

\* \* \* \* \*